United States Patent
Schmieding et al.

(10) Patent No.: US 9,326,844 B2
(45) Date of Patent: May 3, 2016

(54) HYBRID DOUBLE BUNDLE ACL/PCL GRAFT CONSTRUCT WITH A SINGLE GRAFT

(71) Applicant: Arthrex, Inc., Naples, FL (US)

(72) Inventors: Reinhold Schmieding, Naples, FL (US); Jacob A. Jolly, Naples, FL (US); Thomas M. DeBerardino, Avon, CT (US); Adrian Wilson, Old Basing (GB)

(73) Assignee: Arthrex, Inc., Naples, FL (US)

( * ) Notice: Subject to any disclaimer, the term of this patent is extended or adjusted under 35 U.S.C. 154(b) by 0 days.

(21) Appl. No.: 14/192,200

(22) Filed: Feb. 27, 2014

(65) Prior Publication Data
US 2014/0243976 A1 Aug. 28, 2014

Related U.S. Application Data

(60) Provisional application No. 61/770,684, filed on Feb. 28, 2013.

(51) Int. Cl.
*A61F 2/08* (2006.01)
*A61B 17/04* (2006.01)

(52) U.S. Cl.
CPC ............ *A61F 2/0811* (2013.01); *A61B 17/0401* (2013.01); *A61B 2017/0417* (2013.01); *A61F 2002/0852* (2013.01); *A61F 2002/0882* (2013.01)

(58) Field of Classification Search
CPC ........... A61F 2/0811; A61F 2002/0852; A61F 2002/0876; A61F 2002/0882
See application file for complete search history.

(56) References Cited

U.S. PATENT DOCUMENTS

| | | | |
|---|---|---|---|
| 7,326,247 | B2 | 2/2008 | Schmieding et al. |
| 7,819,917 | B2 | 10/2010 | Schmieding et al. |
| 8,333,802 | B2 | 12/2012 | Dougherty |
| 8,366,744 | B2 | 2/2013 | Bojarski et al. |
| 8,439,976 | B2 | 5/2013 | Albertorio et al. |

(Continued)

FOREIGN PATENT DOCUMENTS

| | | |
|---|---|---|
| EP | 1 108 401 A1 | 6/2001 |
| EP | 2 238 944 A2 | 10/2010 |
| EP | 2 311 383 A1 | 4/2011 |
| EP | 2 455 002 A1 | 5/2012 |
| WO | WO 2011/003002 A2 | 1/2011 |
| WO | WO 2012/154922 A2 | 11/2012 |

OTHER PUBLICATIONS

D. Slullitel et al., "Double-Bundle "All-Inside" Posterior Cruciate Ligament Reconstruction." Arthroscopy Techniques, vol. 1 No. 2, pp. e141-e148, Dec. 2012.
D.A. Frank et al., "Hybrid Anterior Cruciate Ligament Reconstruction: Introduction of a New Technique for Anatomic Anterior Cruciate Ligament Reconstruction." Arthroscopy: The Journal of Arthroscopic and Related Surgery, vol. xx, No. x, pp. 1.e1-1.e5, 2007.
T. J. Nancoo et al., "TransMedial All-Inside Posterior Cruciate Ligament Reconstruction Using a Reinforced Tibial Inlay Graft." Arthroscopy Techniques, vol. 2, No. 4, pp. e381-e388, Nov. 2013.
Arthrex Graftlink All Inside ACL Reconstruction with ACL Tightrope ABS, Surgical Technique, 2012.

*Primary Examiner* — Yashita Sharma
*Assistant Examiner* — Daniel Bissing
(74) *Attorney, Agent, or Firm* — Blank Rome LLP

(57) ABSTRACT

Techniques and reconstruction systems for fixation of bone to bone, or soft tissue to bone, that allow a double-bundle type construct with only three tunnels, a single graft and individual tensioning in each of the three tunnels. Alternative double-bundle ACL/PCL fixation techniques are provided that employ a double-bundle type construct with only a single graft and three tunnels/sockets. The double-bundle ACL and PCL techniques and constructs allow individual tensioning of each of the bundles (e.g., tensioning of each of the anteromedial (AM) and posterolateral (PL) bundles of the ACL) and eliminate the need for additional fixation devices (for example, interference screws) to secure the bundles within the bone tunnels/sockets.

9 Claims, 14 Drawing Sheets

(56) References Cited

U.S. PATENT DOCUMENTS

| | | |
|---|---|---|
| 8,460,379 B2 | 6/2013 | Albertorio et al. |
| 8,591,544 B2 | 11/2013 | Jolly et al. |
| 8,591,578 B2 | 11/2013 | Albertorio et al. |
| 8,790,401 B2 | 7/2014 | Schmieding et al. |
| 2007/0191853 A1* | 8/2007 | Stone ............... A61B 17/1675 606/79 |
| 2009/0018654 A1* | 1/2009 | Schmieding et al. ...... 623/13.14 |
| 2010/0256677 A1* | 10/2010 | Albertorio ......... A61B 17/0401 606/232 |
| 2010/0268273 A1* | 10/2010 | Albertorio ......... A61B 17/0401 606/232 |

\* cited by examiner

HYBRID DOUBLE BUNDLE ACL/PCL GRAFT CONSTRUCT WITH A SINGLE GRAFT

CROSS-REFERENCE TO RELATED APPLICATIONS

This application claims the benefit of U.S. Provisional Application No. 61/770,684 filed Feb. 28, 2013, the disclosure of which is incorporated by reference in its entirety herein.

FIELD OF THE INVENTION

The present invention relates to the field of surgery and, more particularly, to ligament repairs and reconstructions such as ACL and PCL repairs and reconstructions and associated fixation devices.

BACKGROUND OF THE INVENTION

Reconstructive surgeries such as double-bundle anterior cruciate ligament (ACL) and posterior cruciate ligament (PCL) are known in the art. Double-bundle ACL and PCL constructs typically require two grafts or a fixation device that can split one graft into two bundles. For example, U.S. Publication No. 2012/0265298 discloses a double-bundle graft with separable strands. A threaded screw is inserted intraarticularly and then between the separable strands to split the strands and provide interference fixation of the graft against radially opposing walls defining the bone tunnel.

Although double-bundle ACL and PCL reconstructions offer significant advantages over single-bundle ACL and PCL reconstructions, it can be difficult for a surgeon to find enough autograft tissue for a double-bundle construct. Additional graft harvesting also causes increased morbidity. The devices that split a single graft into two bundles further fail to allow individual tensioning of the bundles. These devices are also difficult to use because they typically require positioning between the graft strands intraarticularly.

SUMMARY OF THE INVENTION

The present invention provides techniques and reconstruction systems for fixation of bone to bone, or soft tissue to bone. The techniques and reconstruction systems allow a double-bundle type construct with only three tunnels, a single graft and individual tensioning in each of the three tunnels.

The devices and methods of ligament reconstruction of the present invention provide alternative double-bundle ACL/PCL fixation techniques that employ a double-bundle type construct with only a single graft and three fixation devices secured in three separate tunnels/sockets. The double-bundle ACL and PCL techniques and constructs of the present invention allow individual tensioning of each of the bundles (e.g., tensioning of each of the anteromedial (AM) and posterolateral (PL) bundles of the ACL) and eliminate the need for additional fixation devices (for example, interference screws) to secure the bundles within the bone tunnels/sockets.

The double-bundle grafts of the present invention are simpler to assemble and complete, and more closely approximate the native ligament development with enhanced reconstruction results. The techniques produce a more anatomically correct ligament reconstruction, particularly in the case of the AM and PL bundles of the ACL, with individual tensioning of each of the bundles and without the need to tension the bundles intraarticularly (i.e., without having to access the bundles from the inside of the joint or even from the tunnels).

These and other features and advantages of the invention will be more apparent from the following detailed description that is provided in connection with the accompanying drawings and illustrated exemplary embodiments of the invention.

DETAILED DESCRIPTION OF THE PREFERRED EMBODIMENTS

Figure 1:
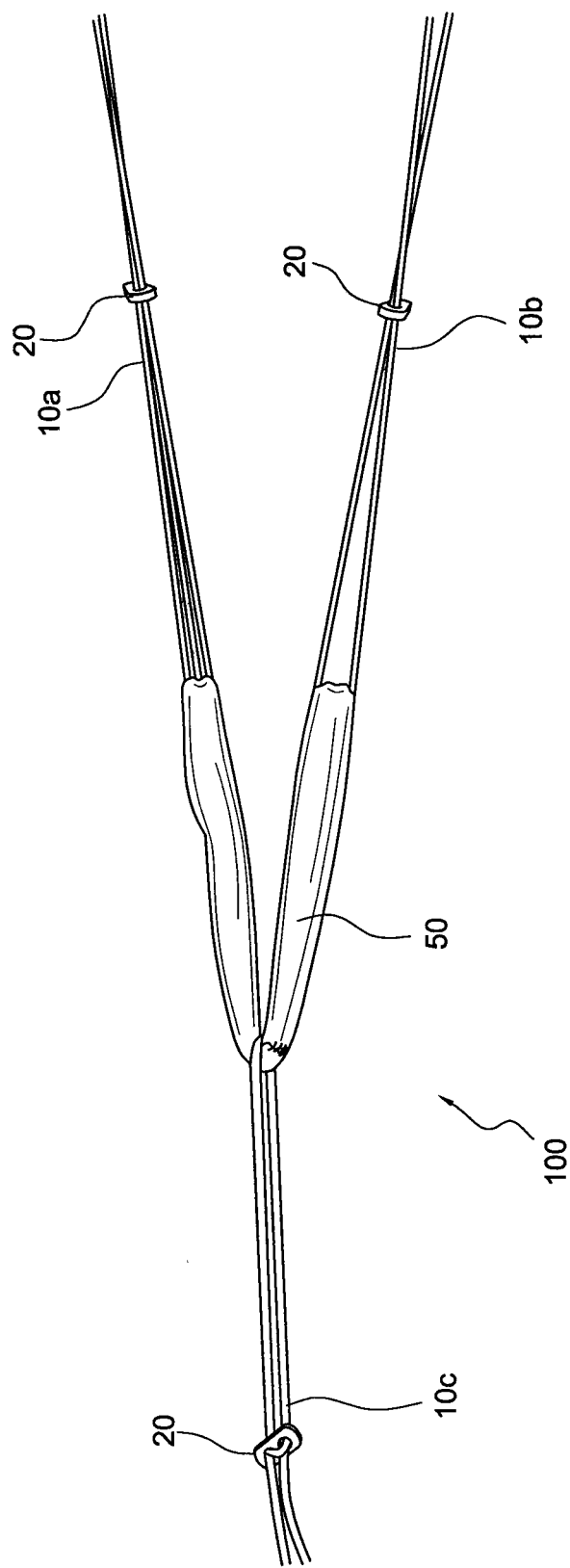
FIG. 1 illustrates an exemplary graft construct with three exemplary adjustable button/loop constructs (each comprising a flexible, adjustable loop attached to a button) according to the present invention.

The present invention provides adjustable fixation systems and reconstruction techniques that employ a continuous loop of tissue (such as soft tissue, graft, tendon, ligament, synthetic material, biological material, or combinations of such materials, among others) attached to three separate and spaced apart fixation devices. The single tissue strand includes three limbs or ends that are fixated with the fixation devices. The fixation devices may include adjustable button/loop constructs, each having a button and a flexible loop connected to the button, the flexible loop having an adjustable length and two adjustable eyesplices that are interconnected, such as disclosed in U.S. Pat. Nos. 8,439,976 and 8,460,379, incorporated by reference herein. Alternatively, the fixation devices may include non-adjustable devices such as an interference screw or suspensory device.

In an exemplary embodiment, the continuous loop of tissue is attached to three separate and independently-adjustable button/loop constructs. In this manner, the adjustable fixation system of the present invention is provided with three separate adjustable button/loop constructs and, thus, with three points of independent tensioning of the loop of tissue (graft or ligament).

In an exemplary-only embodiment, a single tissue strand (for example, a single semitendinosus strand) is looped through two separate adjustable button/loop constructs (for femoral fixation) and one adjustable button/loop construct (for tibial fixation) to form a V-shaped semitendinosus graft with three different attachment and/or tensioning points. The tibia loop allows equal bundle tensioning.

According to another exemplary-only ACL reconstruction, and as described in more detail below, a single loop of tissue is attached to three adjustable button/loop constructs to provide a Y-shaped ACL construct. Two arms (links or ends) of the Y-shaped construct (i.e., the arms that replicate the AM and PL bundles of the ACL construct) are provided in two different sockets/tunnels in the femur (each with an attached adjustable button/loop construct). The third arm (link or end) of the Y-shaped construct is formed by the actual flexible loop of the adjustable button/loop construct and is provided into a socket/tunnel in the tibia. Subsequent to the insertion of the Y-shaped ACL construct into the three sockets/tunnels, tensioning of the final construct may be achieved on both the femoral and tibial sides by simply adjusting the length of each of the continuous suture loops of the three adjustable button/loop constructs.

In yet another exemplary-only embodiment, a pre-constructed allograft construct is provided that allows loading of implants (such as the BTB TightRope® or Open TightRope® ABS) into the loops.

The present invention also provides a method of ligament reconstruction by inter alia the steps of: attaching three separate fixation devices to a single tissue strand; and securing each of the three separate fixation devices to a different bone tunnel or socket.

An exemplary-only method of ligament reconstruction such as ACL or PCL fixation according to the present invention comprises the steps of: (i) forming three bone sockets/tunnels in femur and tibia; (ii) providing an adjustable fixation system including a single loop of tissue (such as graft or tendon) attached to three adjustable and independent button/loop constructs (each of the button/loop constructs including a button and a loop of flexible material, the loop having an adjustable length and adjustable perimeter); (iii) advancing the button/loop constructs with the attached tissue (graft or tendon) through the bone sockets/tunnels; and (v) securing the tissue (graft or tendon) within the bone sockets/tunnels by independently and separately adjusting the length of each of the three loops of flexible material having an adjustable length.

Referring now to the drawings, where like elements are designated by like reference numerals, FIGS. 1-16 illustrate various components of adjustable fixation system 100, 200 of the present invention comprising three self-locking adjustable button/loop constructs 10a, 10b, 10c which allow tissue 50 to be fully inserted and seated into bone sockets/tunnels (for example, two femoral tunnels and one tibial tunnel). FIGS. 3-12 illustrate exemplary steps of a method of forming (assembling) exemplary graft construct 200 of the present invention. FIGS. 13-16 illustrate exemplary steps of a method of ACL reconstruction with the graft construct 200.

Although, for simplicity, reference to tissue 50 will be made in this application as to graft 50, the invention is not limited to this exemplary-only embodiment and contemplates embodiments wherein tissue 50 may be any soft tissue, tendon, ligament, synthetic material, biological material, or combinations of such materials, among others, and as known in the art.

Graft construct 100 (FIG. 1), 200 (FIGS. 12 and 14) includes single graft 50 attached to (for example, looped over) three different fixation devices, for example, three button/loop constructs 10a, 10b, 10c to form a construct having a letter "Y" configuration. Graft 50 attached to (secured to) the three adjustable loops is then pulled into bone tunnels/sockets, as detailed below. Button/loop constructs 10a, 10b with attached graft 50 are secured into two femoral tunnels/sockets. Button/loop construct 10c is secured into a tibial tunnel/socket. The tibial construct allows equal bundle tensioning of the two arms of graft 50 secured into femoral tunnels/sockets (forming a V-shaped graft).

Figure 2:
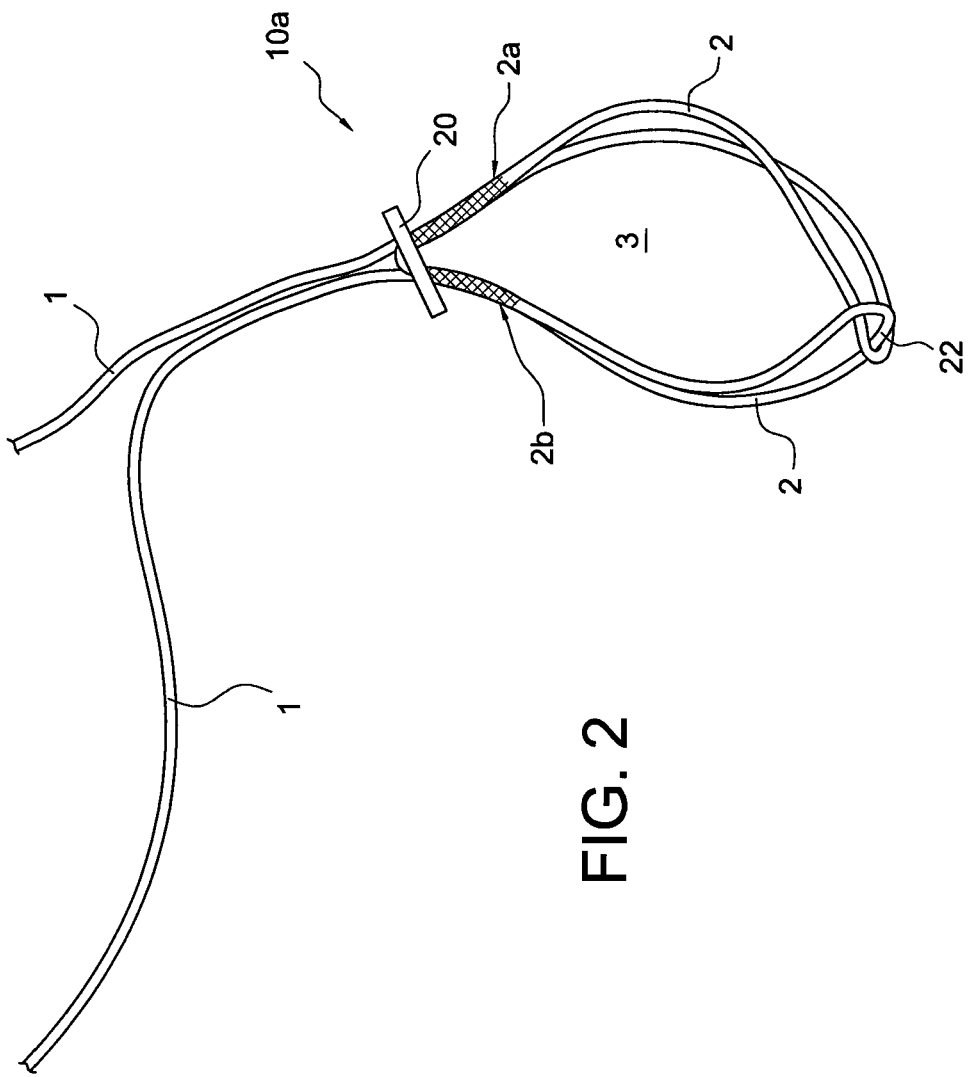
FIG. 2 illustrates one of the three exemplary flexible, adjustable button/loop constructs of the system of FIG. 1.

FIG. 2 illustrates an exemplary fixation device that may be used with the graft 50 to form graft construct 100, 200. Exemplary button/loop construct 10a may be used with the single-strand looped graft 50 to form fixation system 100, 200 of the present invention, and as detailed below. Details of the button/loop construct 10a (and also regarding the formation/assembly of the self-locking adjustable construct 10a) are set forth in U.S. Pat. No. 8,460,379, the disclosure of which is incorporated in its entirety by reference herewith. Self-locking adjustable knotless construct 10a consists of button 20 and flexible material 1 with two adjustable eyesplices 2 that are interconnected to form one adjustable loop 3. The button provides cortical bone fixation of the graft. The loop has an adjustable length (with an adjustable perimeter) and is connected to (supports) tissue such as a graft or ligament. By pulling on the free braid strands 1, the individual eyesplices 2 constrict and, in turn, reduce the loop length of loop 3. In order for loop 3 to elongate, a force needs to be applied interior to one or both of the eyesplices 2 to elongate the individual loops.

To form adjustable, button/loop construct 10a, flexible strand (braid) 1 is first passed through the button 20 and the strands of the braid are looped around one another. Each end of the braid is spliced through itself, traveling in the direction back towards the original hole passed through in button 20. Each end of the braid is passed through the opposite button hole and down towards interconnected braid loops 2. The final construct 10a with eyesplice interconnection 22 is shown in FIG. 2.

Each of the button/loop constructs 10a, 10b, 10c shown in FIG. 1 is a strong locking mechanism (a four-point knotless locking mechanism shown in FIG. 2) that resists slippage and offers stronger pull-to-failure than anatomical failure load. The button/loop constructs 10a, 10b, 10c are knotless, self-locking, adjustable constructs consisting essentially of a button/loop construct having a button and flexible, adjustable loop connected to the button, the flexible, adjustable loop having an adjustable length, the flexible, adjustable loop having two ends, two splices and two adjustable independently-formed loops that are interconnected.

Figure 10:
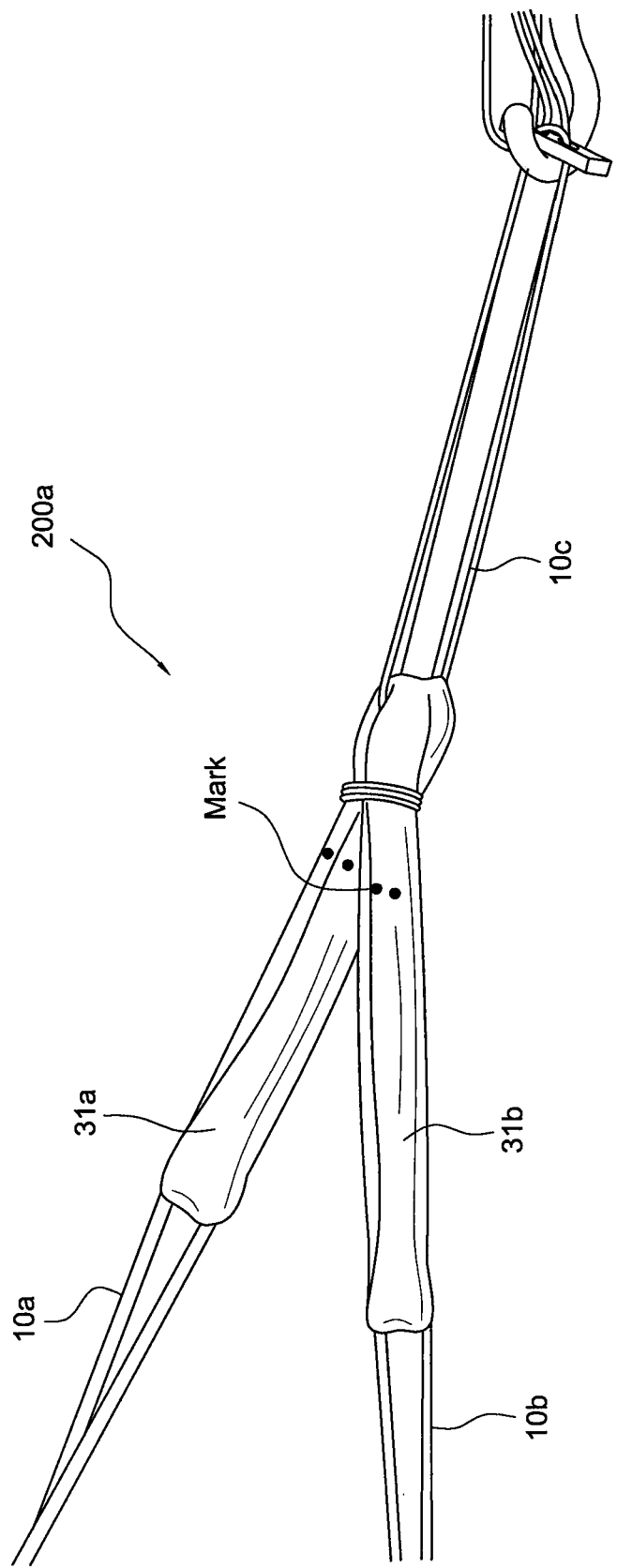
Figure 11:
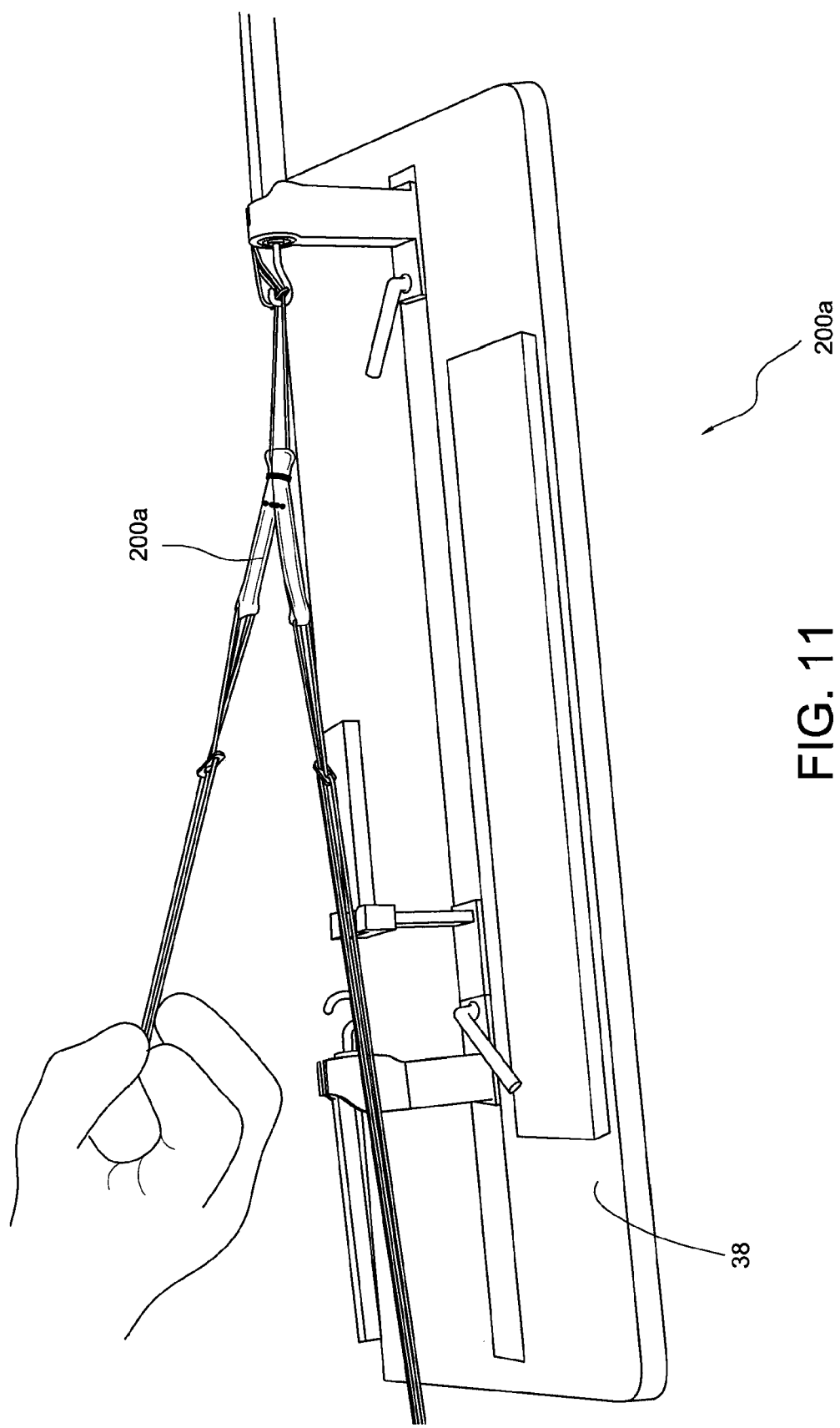
Figure 12:
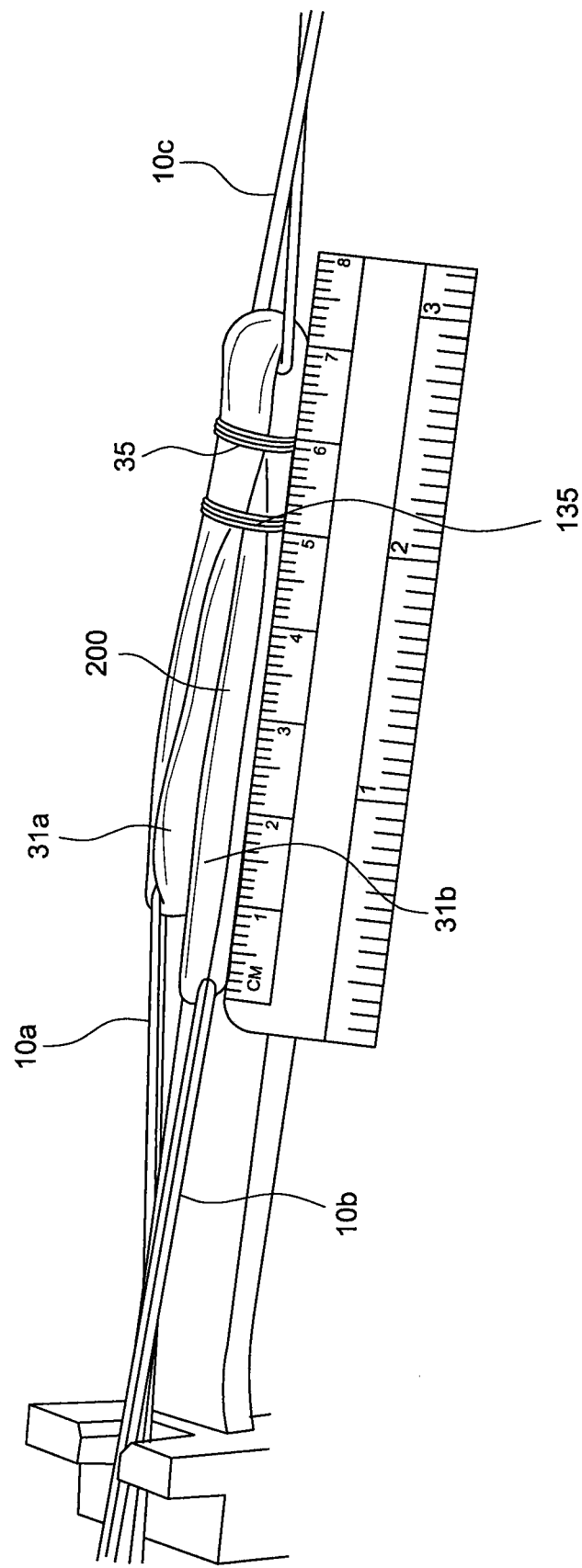

FIGS. 3-12 illustrate exemplary steps of a method of forming exemplary graft construct 200 of FIG. 12. Although the embodiment below will be described with reference to a single tissue strand attached to three fixation devices in the form of self-locking adjustable button/loop constructs 10a, 10b, 10c, the invention is not limited to this exemplary-only embodiment. Thus, the invention contemplates embodiments where a single tissue strand is attached to three separate fixation devices wherein one or more of the self-locking adjustable button/loop constructs are replaced by non-adjustable fixation devices, for example, interference devices such as screws and/or suspensory-type devices.

As detailed below, graft 50 is first attached to two self-locking adjustable button/loop constructs 10a, 10b. Subsequently, an additional adjustable button/loop construct 10c is attached to the single graft 50 so that the flexible loop of construct 10c contacts the graft at a location about half the length of the graft 50, as shown in FIG. 1, for example. Graft 50 may be directly looped over (passed through) the adjustable loops of button/loop constructs 10a, 10b, 10c and then inserted and secured within the bone tunnels/sockets so that the adjustable loops extend between a plurality of bone tunnels/sockets and secure at least a first bone to a second bone.

Figure 3:
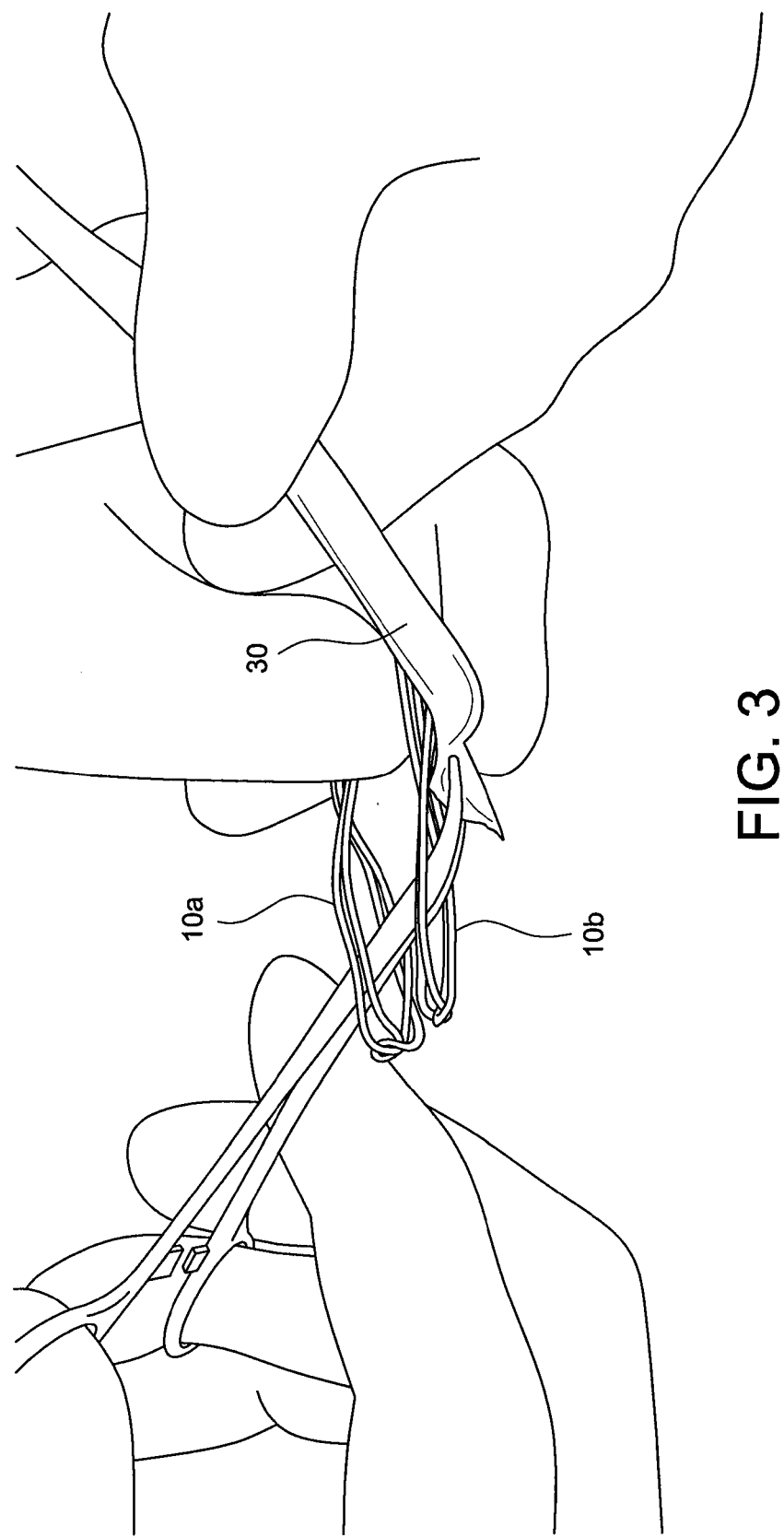
FIGS. 3-12 illustrate exemplary steps of a method of assembling an exemplary graft construct of the present invention.

FIG. 3 illustrates how a single tissue or graft 30 (for example, a single semitendinosous tendon) is passed through two button/loop constructs 10a, 10b (two ACL TightRope® constructs) and fashioned into a loop 31 of about 13 cm long.

Figure 4:
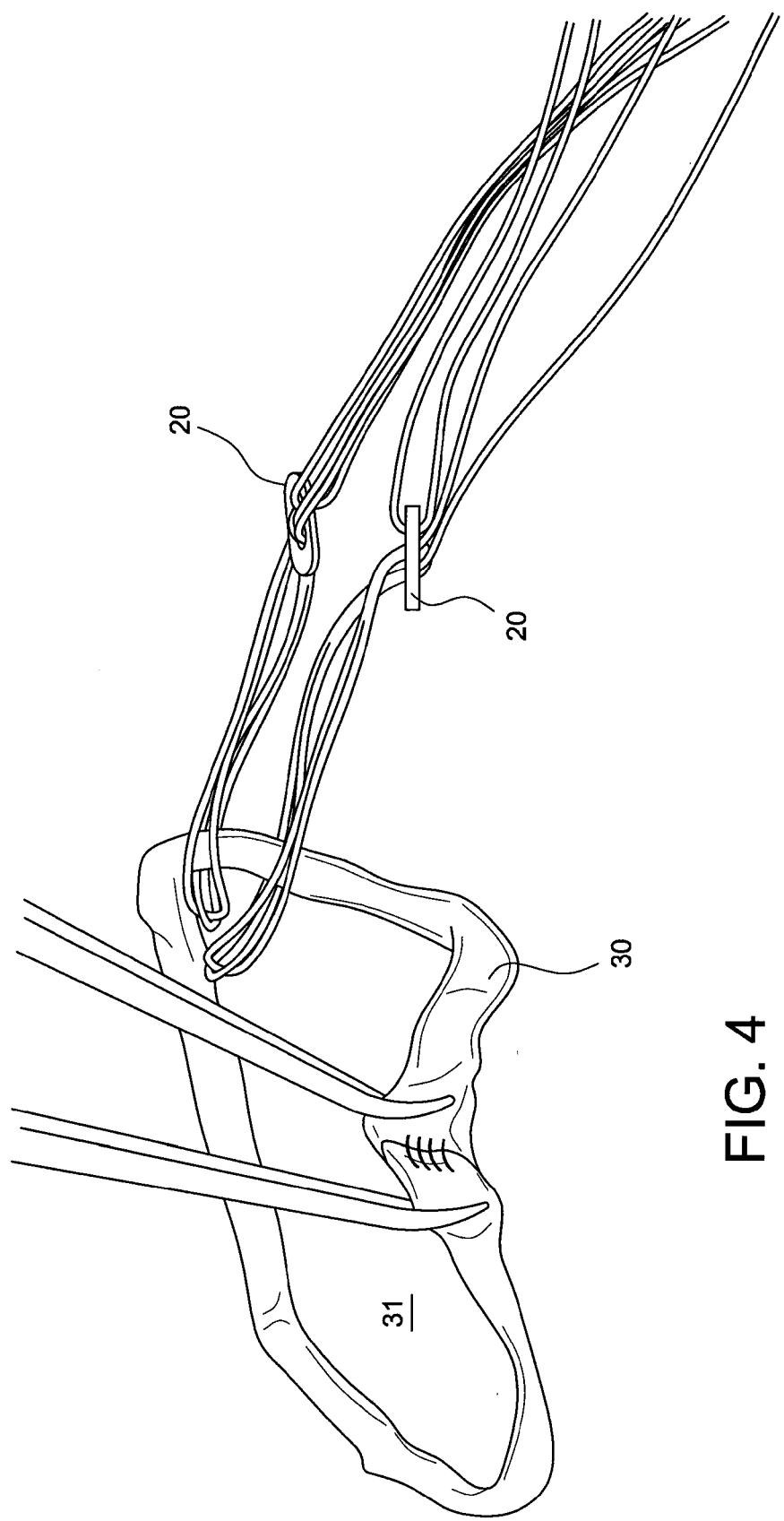

FIG. 4 shows how the ends of the single tissue 30 are brought together (stitched together) with a flexible strand (such as suture, for example) to form loop 31. The graft ends may be brought together by stitching with a single #2 FiberLoop® after passing the graft through two ACL TightRopes®. Alternatively, approximately 2 cm of each graft end may be stitched with one #2 FiberLoop® and one #2 TigerLoop® and then brought together.

Figure 5:
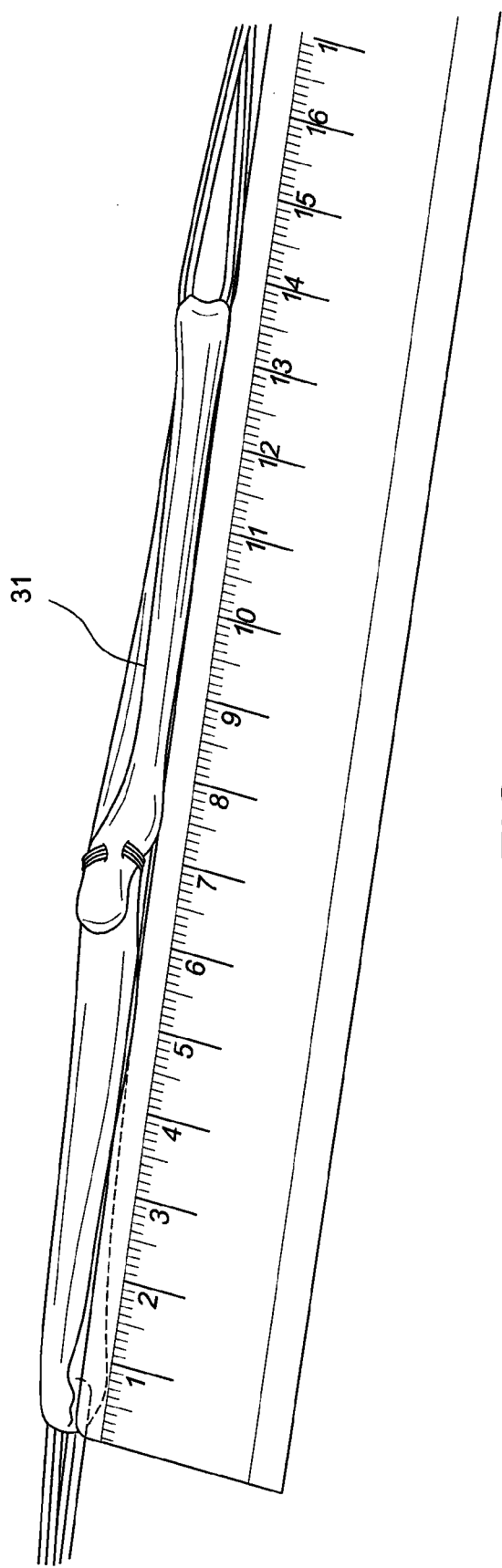

FIG. 5 shows the length of the folded loop 31 (which is about the diameter of the loop 31) of about 13 cm against the ruler.

Figure 6:
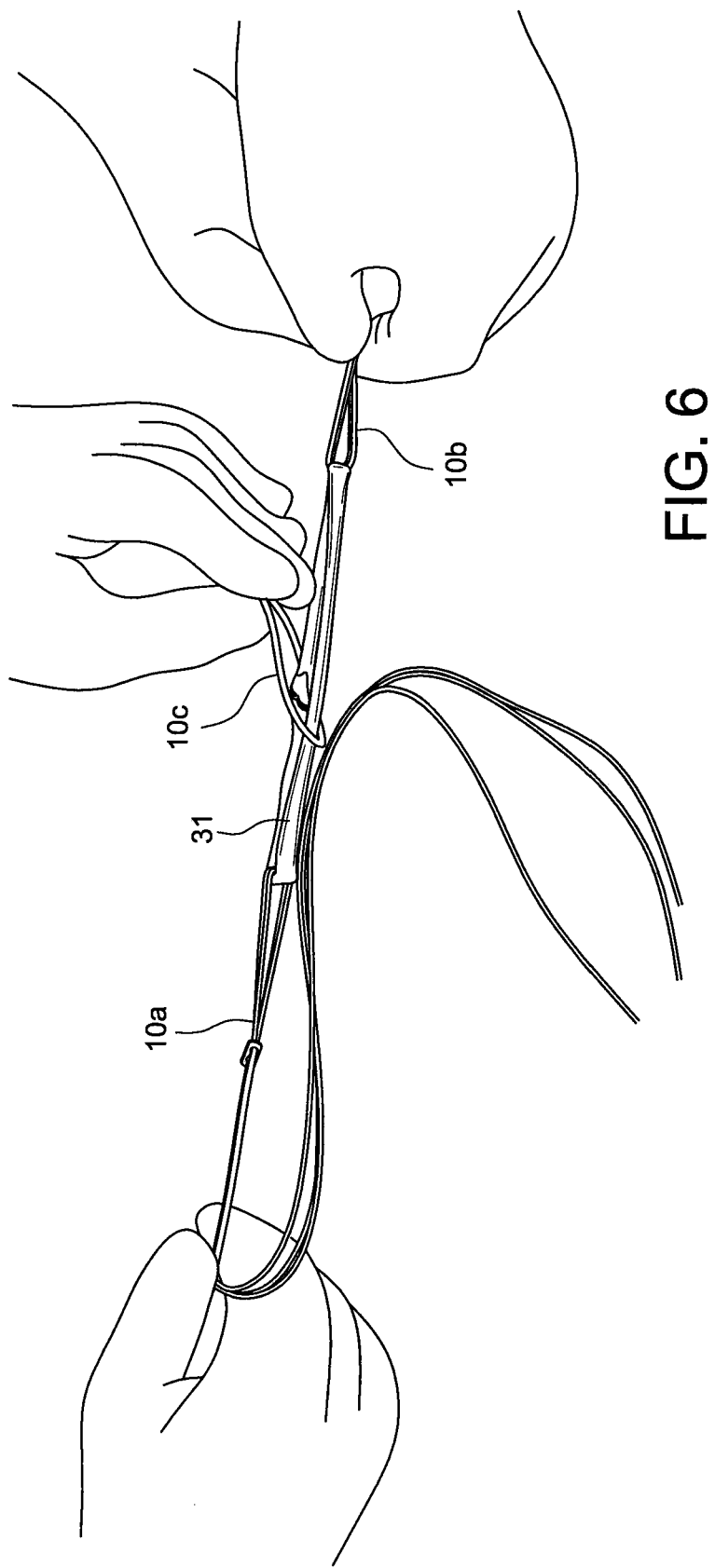

FIG. 6 illustrates how the tendon loop 31 is passed through a third button/loop construct 10c (a third ACL TightRope®) to create a quadrupled-tendon tibial end and two double-tendon femoral ends. The third button/loop construct 10c is loaded about in the middle of the loop construct 31.

Figure 7:
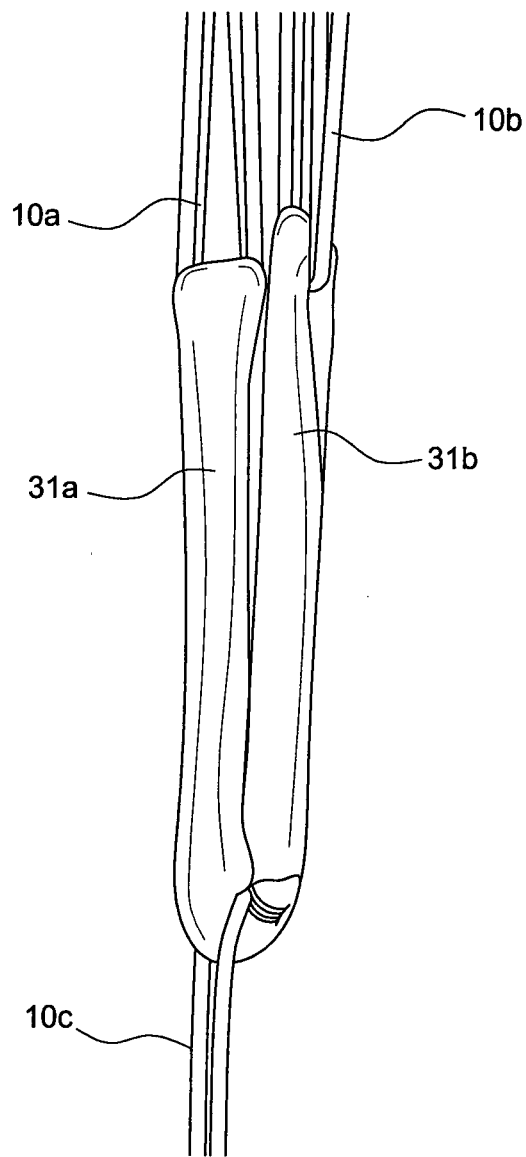

FIG. 7 shows how the femoral ends are adjusted so that AM bundle 31b is about 0.5 cm longer than the PL bundle 31a before the tibial end is secured with flexible strand such as FiberWire® suture.

Figure 8:
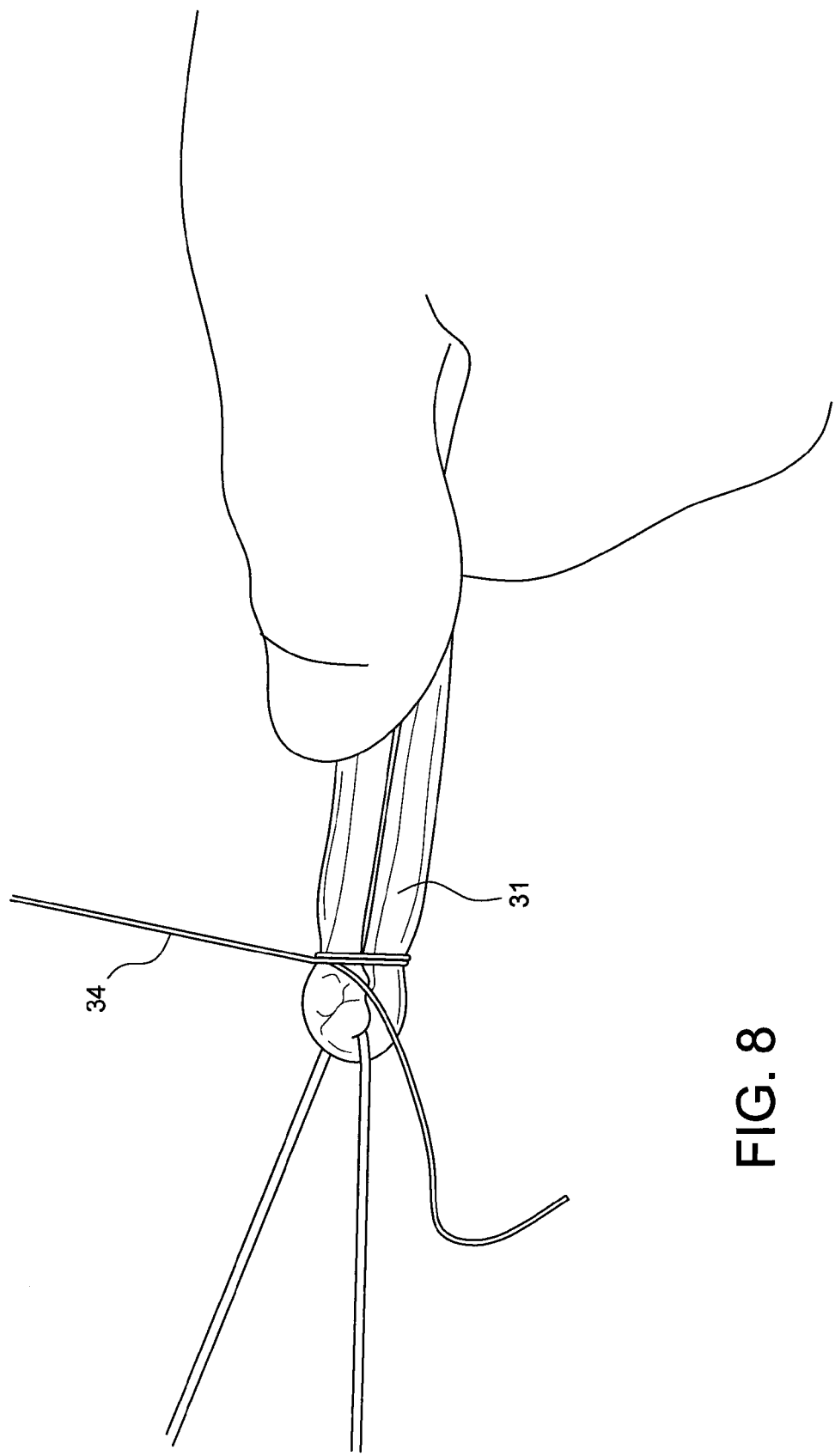
Figure 9:
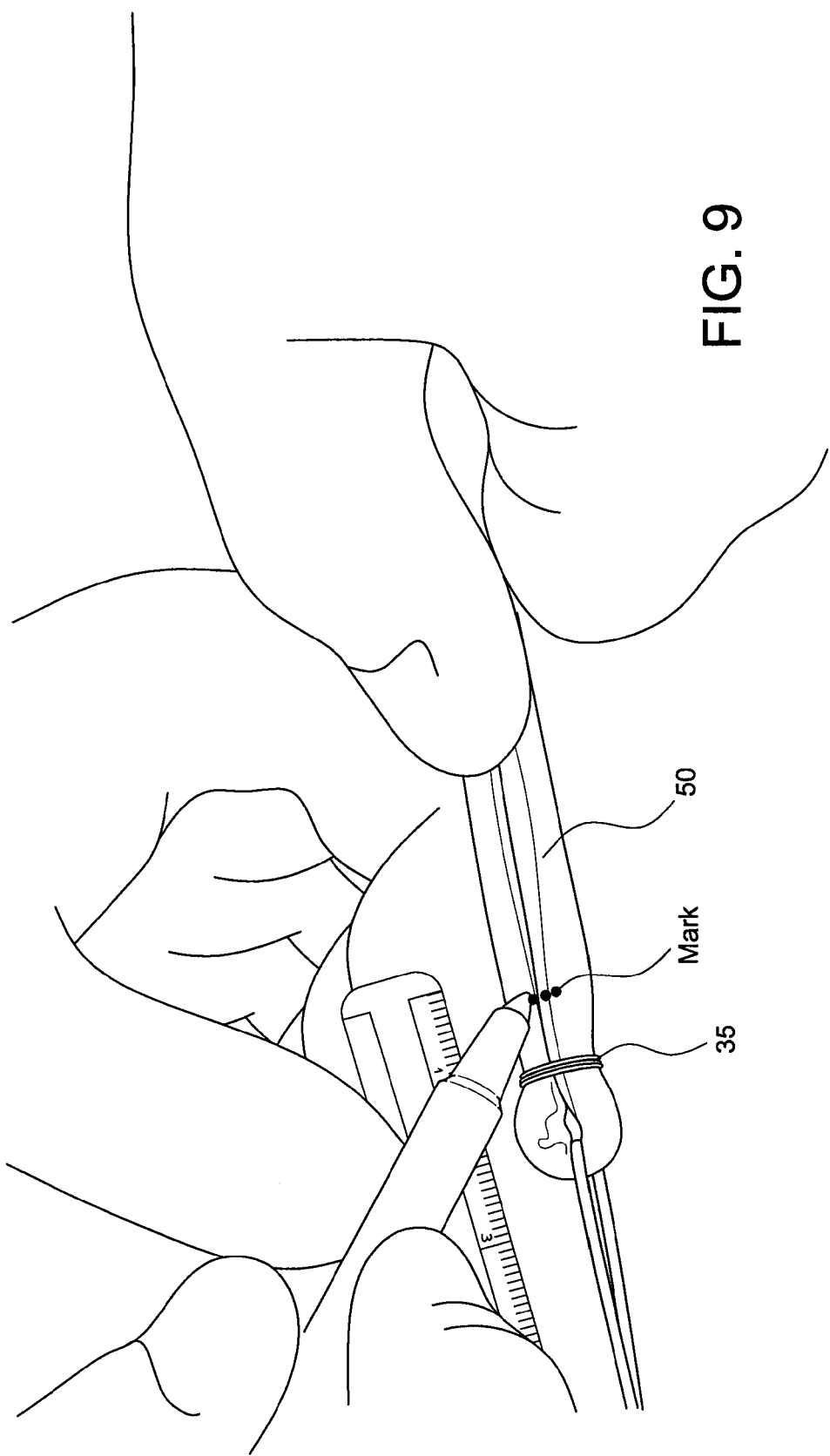

FIG. 8 illustrates the common tibial end with both strands being brought together (stitched, for example with flexible strand 34). This step may include conducting a series of suture passes as detailed and described in GraftLink® preparation to form graft 50 attached to three suspensory devices 10a, 10b, 10c. Suture pattern 35 formed by the series of suture passes is shown in FIG. 9. This step may be conducted in a GraftLink® prep station and may include the following steps:
1. Place the first stitch;
2. Using a "buried knot" technique, start from the inside of the graft and place the needle through the first two graft limbs;
3. Wrap the suture around the graft then place the needle through the second set of graft limbs from outside/in;
4. Tension the suture and tie a knot to secure the stitch;
This may be repeated on either end of the graft for a total of two stiches on each end;
The GraftLink® Graft Prep Attachments may be used for tensioning by simply pulling on one side until the desired tension is obtained, as read on the tensionmeter;
The FiberLoop® whipstitch sutures may be cut off or used as supplemental fixation.

FIG. 9 also shows how the tibial end is marked about 2 cm from its end.

FIG. 10 shows exemplary graft construct 200 of the present invention.

FIGS. 11 and 12 show how the graft construct 200 is loaded onto a graft preparation station 38 so that remaining sutures are inserted under tension. The AM and PL bundles 31b, 31a are tensioned. FIG. 12 illustrates the final graft construct 200 which is measured prior to insertion.

In additional embodiments, to form final graft construct 100, 200 a single graft 30 may be first passed through, and then folded over, loop 3 of construct 10a. The folded graft may then be attached to (passed through) loop 3 of construct 10c. Finally, ends of the graft may be attached to (and secured by suturing, for example, or by any other method) to loop 3 of construct 10b. In this manner, the final assembly 100, 200 comprises a continuous loop of a single graft attached to three different adjustable button/loop constructs 10a, 10b, 10c.

The reconstruction system of the present invention is a graft construct that is an adjustable fixation system. The graft construct includes button/loop constructs with flexible, adjustable loops connected to tissue (for example, soft tissue, graft, tendon, ligament, synthetic material, bone, or combinations of such materials, among others). The tissue may be directly looped over the flexible, adjustable loops for insertion into bone tunnels or sockets. Alternatively, and if desired in certain applications, the tissue may be looped over a tissue supporting device (such as a wedge, anchor, plug, implant, for example) that is connected to the flexible, adjustable loop for further insertion into bone tunnels or sockets. If employed, the tissue supporting device (e.g., the wedge, implant, anchor or plug) also occludes the socket/tunnel to prevent fluid extravasation and minimizes micromotion of the tissue (graft) at the bone orifice/graft interface which may lead to tunnel widening. In other embodiments, the tissue may be provided as a pre-constructed tissue that is sutured, for example, to form a tissue construct having a "Y" configuration and being provided with three independent tissue loops. The pre-constructed tissue allows loading of implants and/or fixation devices into the loops.

Figure 13:
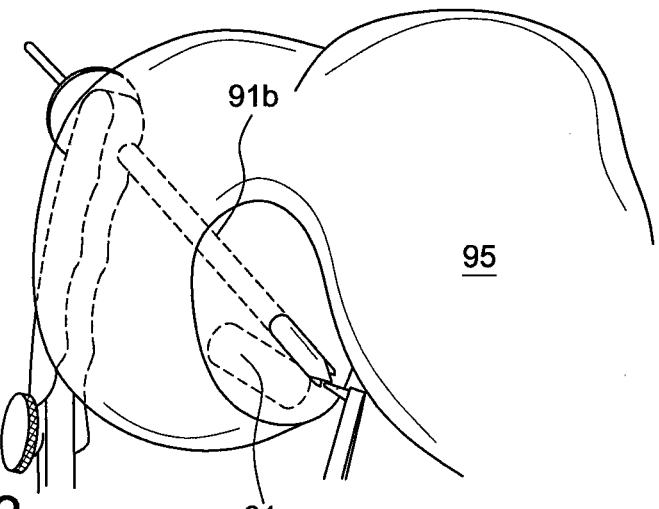
FIGS. 13-15 illustrate exemplary steps of a method of ACL reconstruction with the exemplary graft construct of FIG. 12.
Figure 14:
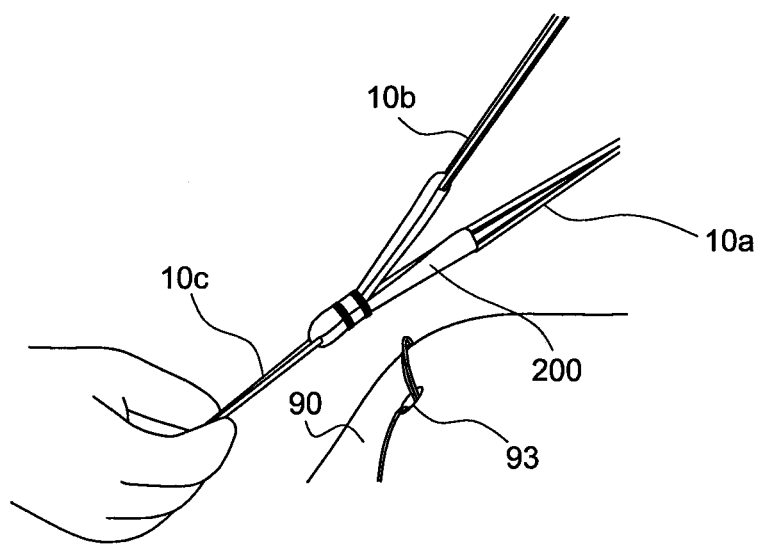
Figure 15:
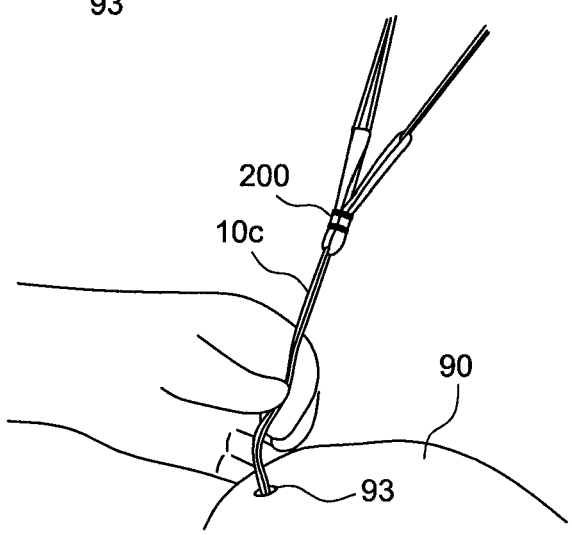
Figure 16:
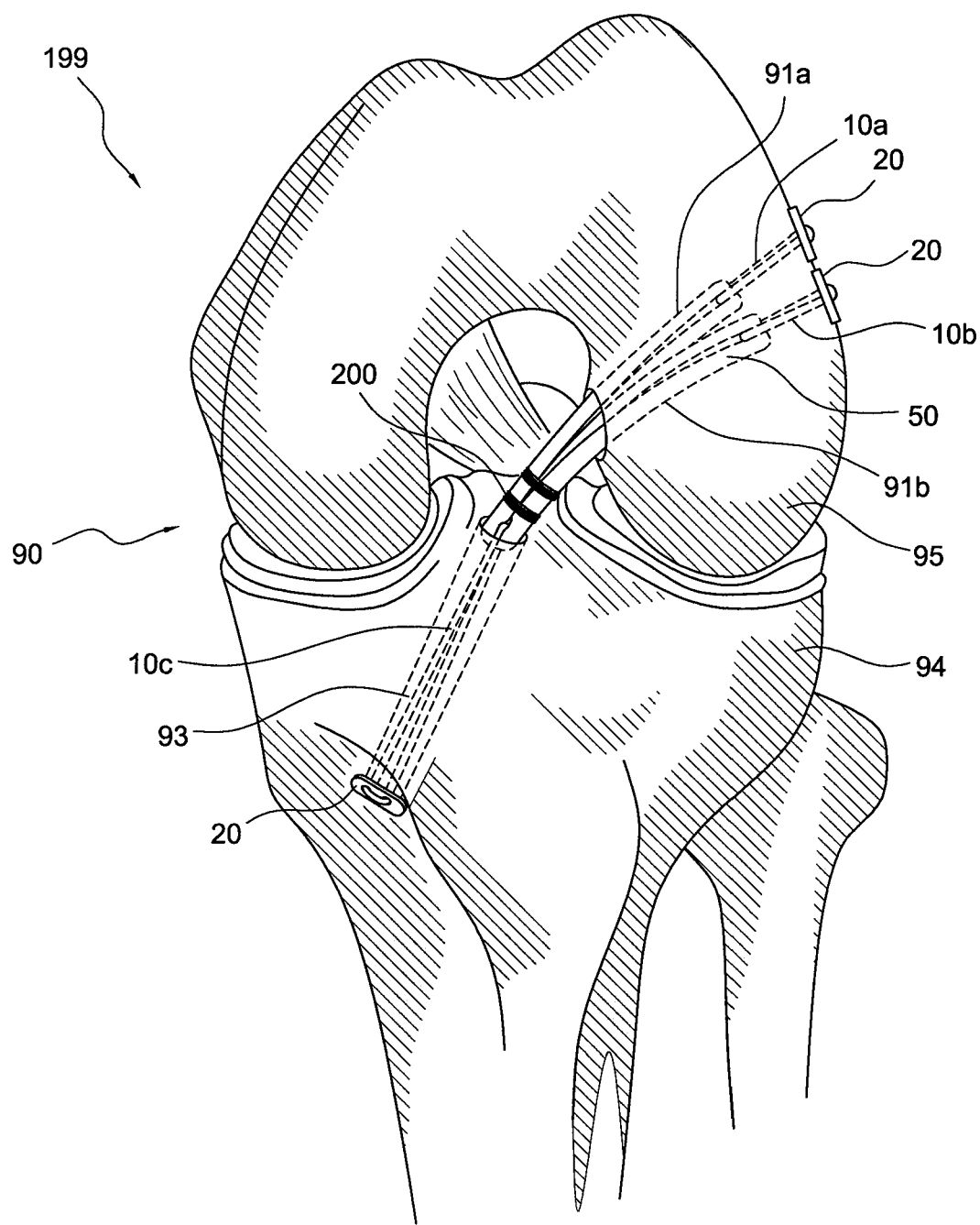
FIG. 16 illustrates a schematic view of the graft construct of FIG. 12 secured within both the femur and the tibia and by a method of the present invention.

FIGS. 13-15 illustrate exemplary steps of a method of ACL reconstruction with the exemplary graft construct 200 of FIG. 12. The method includes the steps of bone tunnel preparation, graft passing and graft fixation. FIG. 16 illustrates a schematic view of the graft construct of FIG. 12 secured within both the femur and the tibia and by a method of the present invention.

FIG. 13 shows the formation of two femoral sockets or tunnels, first and second femoral sockets 91a, 91b (the AM and PL femoral sockets 91a, 91b). These sockets may be formed by any method known in the art, for example, by employing either the medial portal technique or from outside/in, or using a FlipCutter® option, i.e., from inside/out, or a transtibial technique. In FIG. 13, the first femoral socket 91a is already formed and the second femoral socket (the PL femoral socket) is formed adjacent to the first femoral socket 91a by using cutter 72 (for example, a FlipCutter® instrument) and by retrodrilling with the FlipCutter®.

The formation of the tibial socket 93 (FIG. 16) in tibia 94 may be conducted by any known method in the art. In an exemplary-only embodiment, an arthroscope is positioned to anterolateral portal and the tibial guide is inserted via the anteromedial portal and positioned. The tibial socket may be also formed by retrodrilling. Loops of suture from all three sockets are pulled through the medial portal.

FIG. 14 shows the graft construct 200 in the proximity of the three sockets of the repair site undergoing ACL reconstruction and according to a method of the present invention. Using a tibial socket suture-snare, for example, the graft construct 200 is pulled through the medial portal and into the tibial socket 93 (FIG. 15). The AM bundle 31b of the graft construct 200 is pulled into the AM femoral socket. The PL bundle 31a is pulled into the PL socket using an exemplary PL suture snare.

The final tensioning of the graft in extension (at about 30 degrees of flexion) may then be conducted. The tibial side is tensioned first, then PLB on the femoral side.

FIG. 16 illustrates a schematic exemplary repair 199 of the present invention with graft construct 200 positioned and secured within three sockets to complete an ACL repair. Reconstruction system 200 is secured in tibia 94 and femur 95 of knee 90. System 200 is introduced and secured into two tunnels 91a, 91b in the femoral side of the knee (usually through an arthroscopic portal) and into one tunnel 93 in the tibia side. Graft 50 is secured into the two femoral tunnels 91a, 91b forming a V-shaped graft. Buttons 20 are pulled out of the bone cortex with passing sutures and self-flip onto the cortex once tension is released on the passing suture. The adjustable flexible loops 3 are shortened by applying tension to the ends 1a, 1b of each of the loops 3 exiting the bone cortex.

Another exemplary graft construct of the present invention is provided as a pre-constructed allograft construct with three arms (loops) that allows for subsequent loading of implants and/or fixation devices (such as the BTB TightRope® or Open TightRope® ABS) into the three loops.

The double-bundle technique of the present invention facilitates strong, adjustable cortical fixation with aperture graft compression, anatomic (double-bundle) graft orientation, and easy graft insertion and positioning. Loop shortening strands 1a, 1b of the flexible strand 1 of each construct 10a, 10b, 10c are used to control and adjust the length of the loops 3 for final graft tensioning.

Although the embodiments above have been described with reference to a particular ACL reconstruction technique, the invention is not limited to this exemplary embodiment and contemplates additional ligament reconstructions such as, for example, PCL reconstructions, among others. The present invention also contemplates embodiments wherein a plurality of self-locking adjustable knotless constructs with adjustable loops are employed for additional tissue positioning and/or tissue adjustment applications, for example, in fixation of bone to bone (such as small joint applications) which employ a tissue attached to two or more fixation devices (for example, two or more buttons) joined by a continuous suture loop.

Although the embodiments and techniques above have been described with particular reference to the fixation of the graft constructs of the present invention within two femoral sockets or tunnels and one tibial socket or tunnel, the invention is not limited to this exemplary-only embodiment and contemplates embodiments wherein the graft constructs 100, 200 may be secured within any number of bone sockets or tunnels, for example, within two tibial sockets and one femoral socket.

The technique of the present invention allows surgeons to perform minimally invasive ACL reconstruction with the benefits of a double bundle graft construct while only harvesting a single hamstring tendon. Anatomic sockets are prepared with an exemplary FlipCutter® instrument and the graft is fixed securely and tensioned with ACL TightRope® implants. The ACL TightRope® construct gives surgeons the unique advantage of independent tensioning of each graft bundle at the desired degree of knee extension.

While the present invention is described herein with reference to illustrative embodiments for particular applications, it should be understood that the invention is not limited thereto. Those having ordinary skill in the art and access to the teachings provided herein will recognize additional modifications, applications, embodiments and substitution of equivalents that fall within the scope of the invention.

What is claimed is:

1. A method of ligament reconstruction, comprising the steps of:
    attaching three separate fixation devices to a single tissue strand, wherein the single tissue strand is folded to form a first tissue strand arm and a second tissue strand arm, wherein the first and second arms each comprise a double tissue bundle;
    inserting and separately securing each of the three separate attached fixation devices to a different bone tunnel or socket, wherein the three fixation devices are button/loop constructs having a button and a flexible, adjustable loop connected to the button, the flexible, adjustable loop having an adjustable length;
    passing the single tissue strand through a first loop of a first button/loop construct, and through a second loop of a second button/loop construct;
    bringing together ends of the single tissue strand to form a tissue loop;
    passing the tissue loop through a third loop of a third button/loop construct, and positioning the third loop at about half length of the tissue loop to form first and second double tissue bundles of the tissue loop;
    securing the first and second double tissue bundles into two separate femoral tunnels or sockets;
    securing the third loop into a tibial tunnel or socket; and
    tensioning at least one of the first, second and third loops to approximate the anatomic double-bundle graft orientation of a native knee ACL or PCL.

2. The method of claim 1, wherein at least one of the two femoral sockets and tunnels, and the tibial tunnel or socket, is formed by retrograde drilling.

3. The method of claim 1, wherein the step of tensioning does not require accessing the tissue strand from inside of a joint, or from the two separate femoral tunnels or sockets or from the tibial tunnel or socket, to adjust tensioning of the construct.

4. The method of claim 1, wherein the single tissue strand is a single semitendinosous tendon and the three fixation devices are secured within two separate femoral tunnels and one tibial tunnel.

5. A method of ligament reconstruction, comprising the steps:
    forming a continuous tissue strand loop with captured first and second suture loop constructs;
    passing the continuous tissue loop through a third suture loop of an adjustable fixation construct to form first and second double tissue bundles;
    securing the first and second double tissue bundles into femoral tunnels or sockets;
    securing the third loop into a tibial tunnel or socket; and
    tensioning at least one of the first, second and third loops to approximate the anatomic double-bundle graft orientation of a native knee ACL or PCL.

6. The method of claim 4, wherein the loop constructs are adjustable loop constructs.

7. The method of claim 5, wherein at least one of the loop constructs is knotless.

8. A method of ligament reconstruction comprising the steps of:
    passing a single continuous tissue strand through a first loop of a first button/loop construct, and through a second loop of a second button/loop construct;
    bringing together ends of the single continuous tissue strand to form a tissue loop;
    passing the tissue loop through a third loop of a third button/loop construct, and positioning the third loop at about half length of the tissue loop to form two bundles of the tissue loop;
    securing the two bundles into two separate femoral tunnels or sockets;
    securing the third loop into a tibial tunnel or socket; and
    tensioning at least one of the first, second and third loops to approximate the anatomic double-bundle graft orientation of a native knee ACL or PCL.

9. The method of claim 7, wherein the loop constructs are adjustable loop constructs.

\* \* \* \* \*